(12) United States Patent
Wang et al.

(10) Patent No.: US 11,462,326 B2
(45) Date of Patent: Oct. 4, 2022

(54) METHOD AND SYSTEM FOR DISEASE QUANTIFICATION MODELING OF ANATOMICAL TREE STRUCTURE

(71) Applicant: Keya Medical Technology Co., Ltd, Beijing (CN)

(72) Inventors: Xin Wang, Seattle, WA (US); Youbing Yin, Kenmore, WA (US); Junjie Bai, Seattle, WA (US); Qi Song, Seattle, WA (US); Kunlin Cao, Kenmore, WA (US); Yi Lu, Seattle, WA (US); Feng Gao, Seattle, WA (US)

(73) Assignee: KEYA MEDICAL TECHNOLOGY CO., LTD., Beijing (CN)

( * ) Notice: Subject to any disclaimer, the term of this patent is extended or adjusted under 35 U.S.C. 154(b) by 305 days.

(21) Appl. No.: 16/906,936

(22) Filed: Jun. 19, 2020

(65) Prior Publication Data

US 2020/0402666 A1 Dec. 24, 2020

Related U.S. Application Data

(60) Provisional application No. 62/863,472, filed on Jun. 19, 2019.

(51) Int. Cl.
*G16H 50/20* (2018.01)
*G06N 3/04* (2006.01)
*G06N 3/08* (2006.01)

(52) U.S. Cl.
CPC .......... *G16H 50/20* (2018.01); *G06N 3/0445* (2013.01); *G06N 3/0454* (2013.01); *G06N 3/082* (2013.01)

(58) Field of Classification Search
USPC .......................... 704/202, 232, 259; 702/19
See application file for complete search history.

(56) References Cited

U.S. PATENT DOCUMENTS

| | | | |
|---|---|---|---|
| 2019/0155993 A1* | 5/2019 | Wilkerson | G06N 5/022 |
| 2019/0200893 A1* | 7/2019 | Grouchy | G06T 3/4007 |
| 2019/0318476 A1* | 10/2019 | Isgum | A61B 6/504 |
| 2020/0303075 A1* | 9/2020 | Krishna | G16H 50/30 |
| 2020/0342958 A1* | 10/2020 | McGovern | C12Q 1/6883 |

* cited by examiner

*Primary Examiner* — Leonard Saint Cyr
(74) *Attorney, Agent, or Firm* — Bayes PLLC

(57) ABSTRACT

A method and system can be used for disease quantification modeling of an anatomical tree structure. The method may include obtaining a centerline of an anatomical tree structure and generating a graph neural network including a plurality of nodes based on a graph. Each node corresponds to a centerline point and edges are defined by the centerline, with an input of each node being a disease related feature or an image patch for the corresponding centerline point and an output of each node being a disease quantification parameter. The method also includes obtaining labeled data of one or more nodes, the number of which is less than a total number of the nodes in the graph neural network. Further, the method includes training the graph neural network by transferring information between the one or more nodes and other nodes based on the labeled data of the one or more nodes.

20 Claims, 8 Drawing Sheets

A bottom-up message passing example. Incoming Edges indicate the children of the node.

METHOD AND SYSTEM FOR DISEASE QUANTIFICATION MODELING OF ANATOMICAL TREE STRUCTURE

CROSS-REFERENCE TO RELATED APPLICATION

This application claims the benefit of priority to U.S. Provisional Application No. 62/863,472, filed on Jun. 19, 2019, the entire contents of which are incorporated herein by reference.

TECHNICAL FIELD

The disclosure relates to medical image processing and analysis and considers the learning problem of disease quantification for anatomical tree structures (e.g., vessels, airway trees or the like), using labeled data (such as ground truth values) available for training.

BACKGROUND

Accurate disease quantifications of anatomical tree structure are useful for precise diagnosis. For example, it has been proved that Fractional Flow Reserve (FFR) is a reliable index for the assessment of the cardiac ischemia. FFR can be measured by pressure wire. Pressure wire measurement is invasive and only one or several values may be measured in the whole tree because of the level of invasiveness. Attempts have been made to estimate FFR using learning-based methods. Such learning based FFR estimation is fundamentally a low-data problem since the ground truth measurements are provided only at one, a few, or several locations. FIG. 1 shows several scenarios with ground-truth FFR values: one point (FIG. 1A), several isolated points (FIG. 1B), or values along one segment (FIG. 1C). With only a small amount of invasive FFR values (measured by pressure wire) available for a training process, it is challenging to provide accurate predictions for the whole coronary artery tree. The existing machine learning based methods rely on simulated FFR values as ground truth for training the model. However, the simulated FFR values are usually calculated by numeric flow simulation based methods, which are time-consuming and too inaccurate for training the machine learning model. Thus, the performance of conventional machine learning-based methods is highly restricted by simulation methods.

SUMMARY

The present disclosure is provided to, among other things, overcome the drawbacks in the conventional methods for disease quantification modeling of anatomical tree structure with learning network. Instead of using the simulated FFR as the ground truth for training the FFR model, a goal of certain embodiments of the present disclosure is to train the FFR model with the measured invasive FFRs directly. The measured invasive FFRs are the most accurate values as the ground truth for training the model compared to the other values (calculated by algorithms) as the ground truths.

In one aspect, a computer implemented method for disease quantification modeling of an anatomical tree structure is provided. The method may include the follows steps for each training image to perform the corresponding training/learning. The method may include obtaining a centerline of an anatomical tree structure from the training image. The method may also include generating, by a processor, a graph neural network including a plurality of nodes based on a graph. Each node of the graph neural network may correspond to a centerline point and edges between the nodes of the graph neural network may be defined by the centerline, with an input of each node being a disease related feature or an image patch for the corresponding centerline point and an output of each node being a disease quantification parameter. Further, the method may include obtaining labeled data of one or more nodes, the number of which may be less than a total number of the nodes in the graph neural network. Still further, the method may include training, by the processor, the graph neural network by transferring information between the one or more nodes and other nodes based on the labeled data of the one or more nodes.

In another aspect, a system for disease quantification modeling of an anatomical tree structure is provided. The system may include an interface and a processor. The interface may be configured to receive training images containing the anatomical tree structure. The processor may be configured to perform the follows steps for each training image. The processor may be configured to obtain a centerline of the anatomical tree structure. The processor may be further configured to generate a graph neural network including a plurality of nodes based on a graph. Wherein each node may correspond to a centerline point and edges between the nodes of the graph neural network may be defined by the centerline, with an input of each node being a disease related feature or an image patch for the corresponding centerline point and an output of each node being a disease quantification parameter. The processor may be further configured to obtain labeled data of one or more nodes, the number of which may be less than a total number of the nodes in the graph neural network. Moreover, the processor is configured to train the graph neural network by transferring information between the one or more nodes and other nodes based on the labeled data of the one or more nodes.

In a further aspect, a non-transitory computer readable medium storing instructions that, when executed by a processor, may perform a method for disease quantification modeling of an anatomical tree structure. The method may include obtaining a centerline of an anatomical tree structure. The method may further include generating a graph neural network including a plurality of nodes based on a graph. Wherein each node may correspond to a centerline point and edges between the nodes of the graph neural network may be defined by the centerline, with an input of each node being a disease related feature or an image patch for the corresponding centerline point and an output of each node being a disease quantification parameter. The method may further include obtaining labeled data of one or more nodes (e.g., from the training image), the number of which may be less than a total number of the nodes in the graph neural network. Moreover, the method may include training the graph neural network by transferring information between the one or more nodes and other nodes based on the labeled data of the one or more nodes.

Use of graph neural networks has demonstrated that, in some circumstances, predictions may be performed from only one or a few data points (such as nodes). The method of certain embodiments of the disclosure may propagate information from labeled data points towards the unlabeled data points. Certain embodiments of the disclosure may use both the implicit representations (such as feature embedding) and explicit relationships (such as graph) for learning disease models of the whole anatomical tree structure. The disclosed method builds a graph where each node corresponds to a point on a centerline of the tree structure. These nodes may be linked via the centerline. The input to each node of the graph may be a vector representation (also referred to as feature embedding) of each node. The disclosed method then generates and uses a dynamic graph neural network to transfer information (message passing) between the nodes with the ground truth values (for example, invasive FFR value) and the nodes without ground truth values. Certain of the disclosed methods and systems have at least the following benefits. Firstly, the disease prediction task is formulated as an interpolation problem on a graph under the deep learning architectures that may rely on supervision from only a few ground truth values, nodes are associated with the points on the centerline of the tree, and edges are defined by the centerline. Secondly, anatomical tree structures have variations, but the disclosed graph neural networks can deal with such variations using dynamic graphs for individuals. Thirdly, the disclosed dynamic graph neural network may learn how to propagate label information from labeled data points towards the unlabeled data points during the optimization process, so as to obtain a well-trained graph neural network regardless of the deficiency of labeled data points.

Moreover, in contrast to the conventional methods, the disclosed system not only considers the points of the centerline independently but also embeds graph structure among all centerline points. With the information propagation of the nodes in the deep memory graph nets, the disclosed framework can seamlessly integrate the information from the centerline points in the whole tree to make an accurate prediction with only limited labeled data. With the spatially close neighbor nodes being considered during learning of the graph neural network, global considerations among nodes may be integrated into the training in such a way that relations between one node and surrounding nodes are considered together with hidden information.

It is to be understood that the preceding general description and the following detailed description are exemplary and explanatory only, and are not restrictive of the invention, as claimed. A given embodiment may provide one, two, more, or all the preceding advantages, and/or may provide other advantages as will become apparent to one of ordinary skill in the art upon reading and understanding the present disclosure.

BRIEF DESCRIPTION OF THE DRAWINGS

In the drawings, which are not necessarily drawn to scale, like reference numerals may describe similar components in different views. Like reference numerals having letter suffixes or different letter suffixes may represent different instances of similar components. The drawings illustrate generally, by way of example, but not by way of limitation, various embodiments, and together with the description and claims, serve to explain the disclosed embodiments. Such embodiments are demonstrative and not intended to be exhaustive or exclusive embodiments of the present method, system, or non-transitory computer readable medium having instructions thereon for implementing the method.

DETAILED DESCRIPTION

Figure 1:
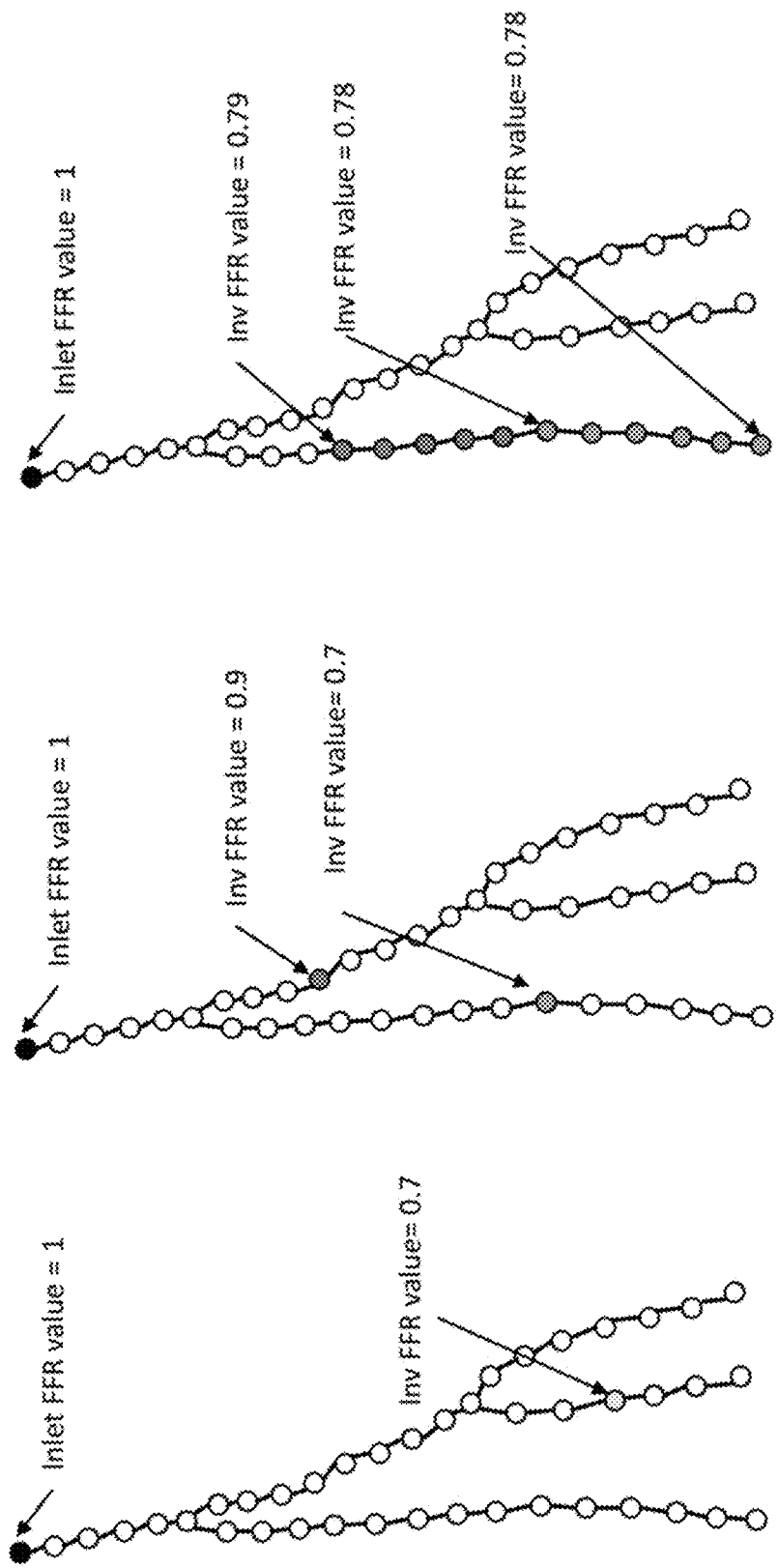
FIG. 1A is a schematic diagram illustrating scenarios with only one centerline point having ground-truth FFR value.
FIG. 1B is a schematic diagram illustrating scenarios with several centerline points having ground-truth FFR values.
FIG. 1C is a schematic diagram illustrating scenarios with multiple centerline points along one segment or path having ground-truth FFR values.

For the purposes of facilitating an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure pertains. In particular, it is fully contemplated that the features, components, and/or steps described with respect to one embodiment may be combined with the features, components, and/or steps described with respect to other embodiments of the present disclosure. The order of steps of the method does not limit to the described or shown one. According to the disclosure, the order of steps may be varied according to actual requirements without departing from the gist of the disclosure. For the sake of brevity, however, the numerous iterations of these combinations will not be described separately herein.

Hereinafter, the technical term "anatomical tree structure" may refer to vessels, airways, and the like with tree structure. The technical term "medical image" may refer to a complete image or an image patch cropped from a complete image in any form including the forms of two dimensional (2D), 2D plus depth, or three dimensional (3D). Although FFR, which is a reliable index for assessment of cardiac ischemia, is mentioned above for describing the process, no limitation to the FFR is intended according to the present disclosure. Instead, the present disclosure is applicable to any disease quantification parameter of any anatomical tree structure.

As described above, because the procedure of measuring FFR by pressure wire is invasive, it is preferable that only a few invasive values may be measured in the whole tree. In some embodiments, only one FFR value may be measured at the inlet. In alternative embodiments, several other scenarios are possible as shown in FIGS. 1A, 1B, and 1C. As shown in FIG. 1A, only one invasive FFR value equal to 0.7 is measured in addition to an inlet FFR value equal to 1. As another scenario, FIG. 1B illustrates two invasive FFR values are measured in addition to an inlet FFR value equal to 1. A scenario where multiple values are measured from a segment or path obtained using pull-back curves using pressure wire, which is invasive, is illustrated in FIG. 1C. The present disclosure proposes to optimize disease quantification model using learning-based methods with only limited FFR value(s) available.

Figure 2:
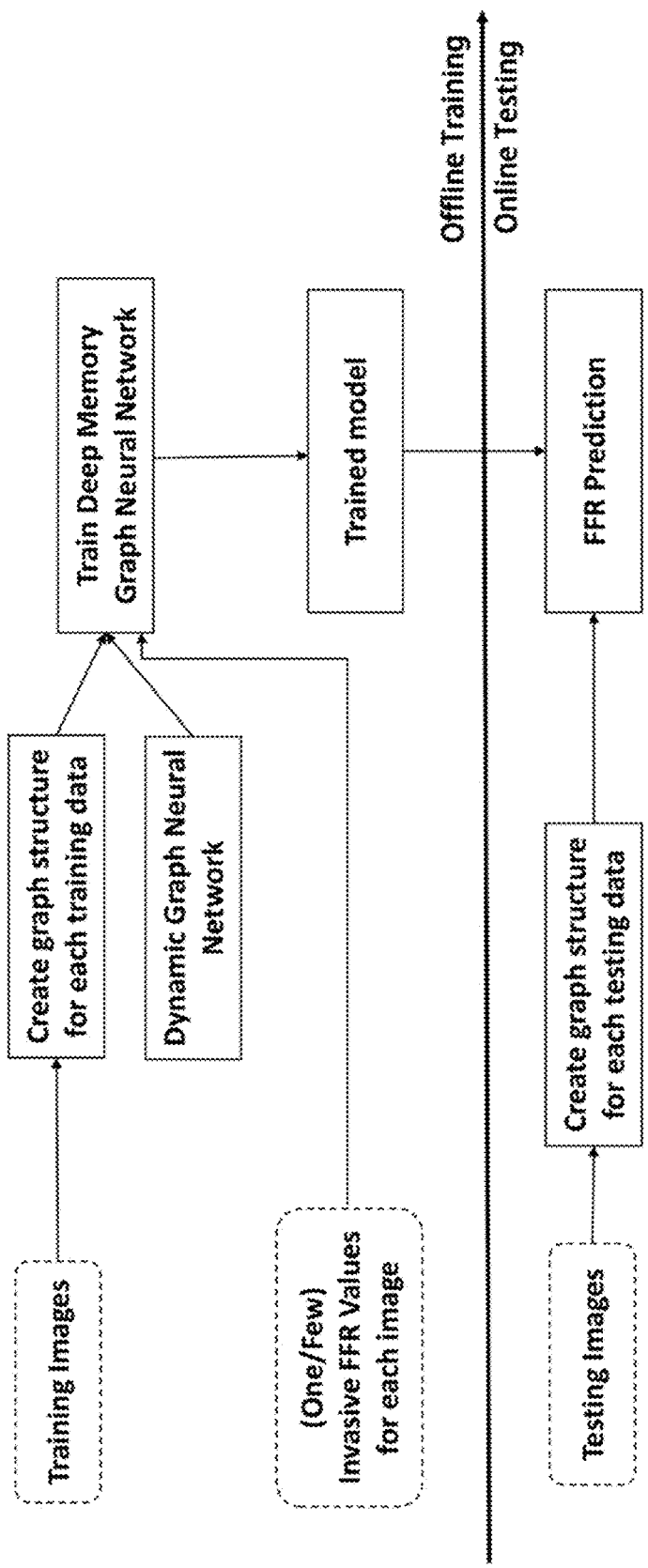
FIG. 2 illustrates an overall framework for FFR (as an example of the disease quantification parameter) prediction with dynamic graph neural network according to an embodiment of the present disclosure.

The framework of an example method according to the present disclosure is illustrated in FIG. 2, including two phases: a training phase as an offline process and a prediction phase as an online process. During the offline training, a database of annotated training data (training images) with ground truth values (as an example of labeled data) is assembled. A graph representation algorithm may be adopted to automatically extract features from the sampled centerline points to create the graph structural representation for each training data. In particular, the dynamic graph neural network may learn to transfer information (message passing) between the nodes with the ground truth values and the nodes without the ground truth values, which will be described below, to obtain a well-trained deep memory graph neural network.

The prediction phase shown as online testing in FIG. 2 is completed online, whereby the disease quantification parameter (e.g., FFR) of the whole tree for an unseen data can be calculated by using the learned model from the offline training phase. In some embodiments, the method may perform the steps for each test image to predict disease quantification parameters along the anatomical tree structure. Upon a test image containing a test anatomical tree structure ("test anatomical tree structure" is used to differentiate from the anatomical tree structure contained by the training image) is received, the processor may extract a test centerline of the test anatomical tree structure. The processor may generate a trained test graph neural network including a plurality of nodes based on the trained model as shown in FIG. 2. In some embodiments, the trained test graph neural network may be generated based on a test graph where each test node corresponds to a test centerline point and edges between the nodes of the graph neural network are defined by the test centerline. A test neural network unit for each test node may follow a graph-template setting of a neural network unit for each node of the trained graph neural network. The term "a graph-template setting of a neural network unit" may refer to a network parameter setting definition with respect to all graphs. Particularly, the network parameters of the neural network unit may be set based on the local graph relationship of the corresponding centerline point using the network parameter setting definition. The network parameter setting definition may define what network parameters of the neural network unit will be used confronting what local graph relationship of the corresponding centerline point. A test disease related feature or a 2D/3D image patch may be extracted for each test centerline point. Disease quantification parameters along the test centerline may then be predicted based on the extracted disease related features or 2D/3D image patches by utilizing the trained test graph neural network.

Figure 3:
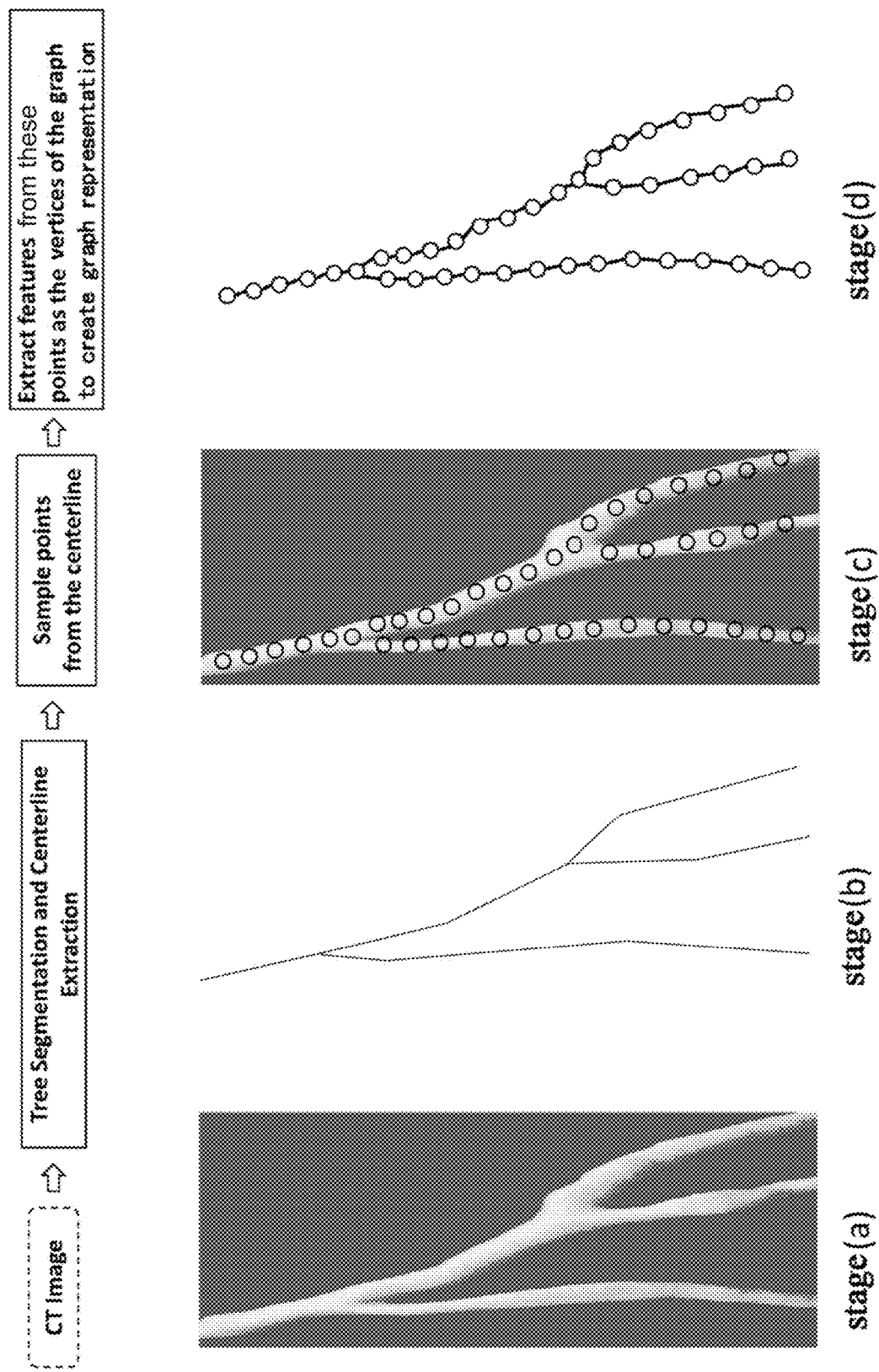
FIG. 3 illustrates a process of creating graph representation from Computed Tomography (CT) image including stage(a)-stage(d) according to an embodiment of the present disclosure.

In some embodiments, the process as shown in FIG. 3 may be used to create graph representation from an image (e.g., CT image) as an input, including stages (a)-(d). At stage(a), the image may be obtained from a training image database. At stage(b), the image of tree structure may be segmented and thus centerline can be extracted for the image. Thereafter, it is possible to sample points from the centerline, as shown in stage(c). Then, at stage(d), features may be extracted from these points as the vertices (nodes) of the graph to create a graph representation. In particular, the features may be disease related features.

For example, an initial artery segmentation (stage(a)) with a centerline (stage(b)) is firstly generated, which could be obtained automatically, semi-automatically or manually. Secondly, points on the centerline are sampled (stage(c)) as the vertex (V) of the graph (G). For each sampled point on the centerline, disease related features can be extracted, which may include but may not be limited to structural features, intensity features, other derived features, or the like. As an example of the structural feature, the geometric features may include any one of radius, areas, stenosis, volumes, length, curvatures, etc. Intensity features may include any one of intensity-related measurements, such as intensity statistic measurements (minimum, maximum, mean, etc.), gradients, etc. The other derived features could be any feature derived based on the tree structures, intensity or even information related to other anatomic structures. For example, if FFR prediction is needed, such features could be pressure drops or resistance estimated using simplified equations.

As can be seen from an example of the architecture at stage(d) of FIG. 3, points on the centerline are linked by edges, which may be undirected. Thus, in the context of certain embodiments of the present disclosure, the technical term "edges," can refer to lines linking two or more nodes. In some embodiments, the edges may also be directed. In particular, the undirected edge may be treated as two directed edges shows that there is a relation or association between two nodes. Generally, directed edges can bring more information than undirected edges. Undirected edges may reflect an underlying anatomical structure, while directed edges may further show information such as flow direction.

In some embodiment, the information can be propagated from the root of the tree to the terminals, and it can also be propagated in the opposite direction (e.g., from terminals to the root of the tree). Stated differently, the information propagation or passing between nodes of the tree structure can be implemented by considering both directions.

According to the present disclosure, the tree T is associated with a graph $G_T=(V,E)$, where nodes $v_i \in V$ correspond to the feature vectors or embedding of the points on the centerline (both with ground truth values and unknown values), and edges $e_i \in E$ correspond to directed or undirected edges between the points. According to the present disclosure, both the implicit representations (i.e. feature embedding) and explicit relationships (i.e. graph) may be fused for learning disease models of the whole anatomical tree structure. According to some embodiments, structural information may be incorporated into disease quantification problem during implementation of the dynamic graph neural network to deal with variations of various anatomical tree structures using dynamic graphs for individuals. According to some embodiments, each node corresponds to a centerline point and edges between the nodes of the graph neural network are defined by the centerline. The input of each node may be a disease related feature or a cropped 2D/3D image patch for the corresponding centerline point, and an output of each node may be a disease quantification parameter. According to the disclosure, the disease prediction task may be formulated as an interpolation problem on a graph under the deep learning architectures that involve supervision from only a few ground truth values.

Figure 4A:
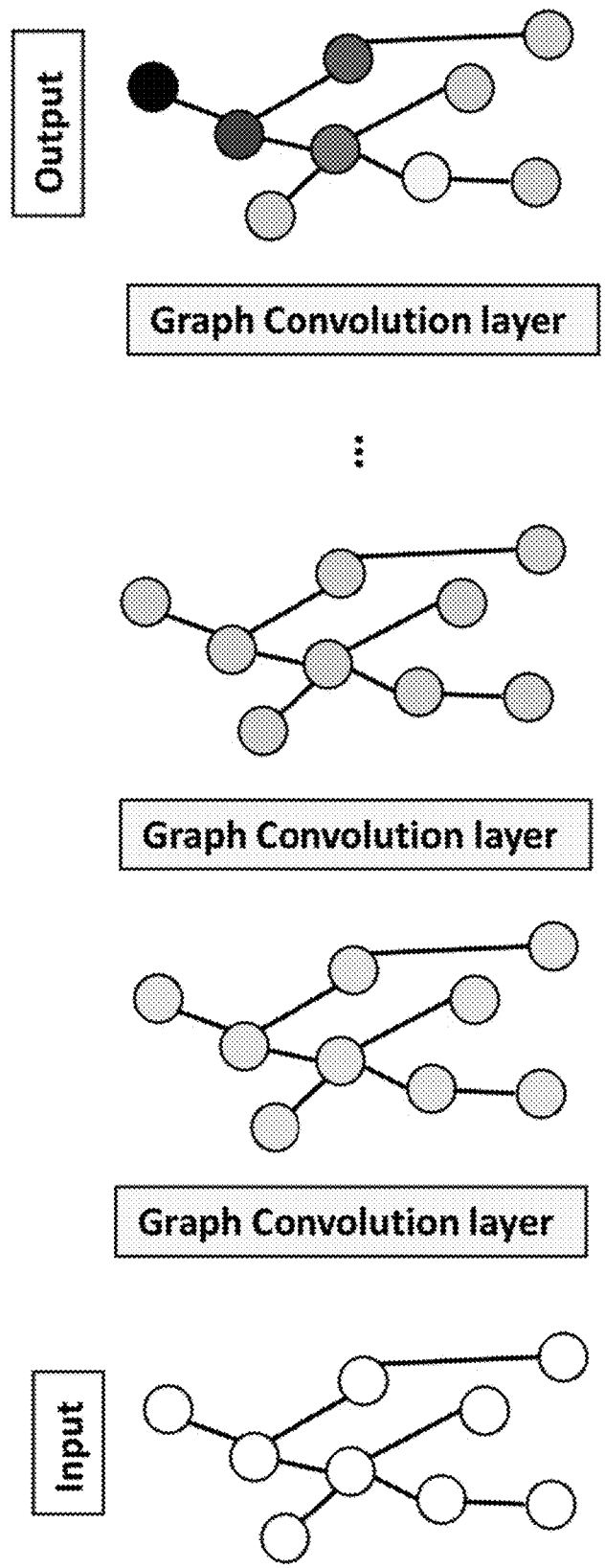
FIG. 4A is a schematic diagram illustrating a graph convolution type of dynamic graph neural network according to an embodiment of the present disclosure.

FIG. 4A illustrates a diagram showing the structure of a Graph Convolution Neural Network (GCN). The goal of GCN may include generalization of Convolution Neural Network (CNN) architectures to non-Euclidean domains (for example, graphs). As shown in FIG. 4A, the graph convolution may define convolutions directly on the graph, whereby a series of convolutional operations can be performed for each node taking a given node's spatially close neighbor nodes into account with graph convolution layers. In this way, global considerations among nodes may be integrated into the training such that relations between one node and surrounding nodes are considered together with hidden information.

The GCN can be a function of the input which may include two components: nodes representation X and an adjacent matrix that indicates the edges among the nodes, the structure of which may be formally expressed as:

$$Z=GCN(X,A),$$

Where $X \in R^{N \times C}$, is the nodes representation, N is the node number, C is the dimension of the feature embedding, A is an adjacent matrix to denote if there are edges between nodes, and Z is the output of the GCN. According to the present disclosure, the adjacent matrix A can be determined by the centerline. According to some embodiments, the adjacent matrix A may be fixed.

Other common methods applicable in CNN can also be used in GCN, such as skipping connection or attention.

Figure 4B:
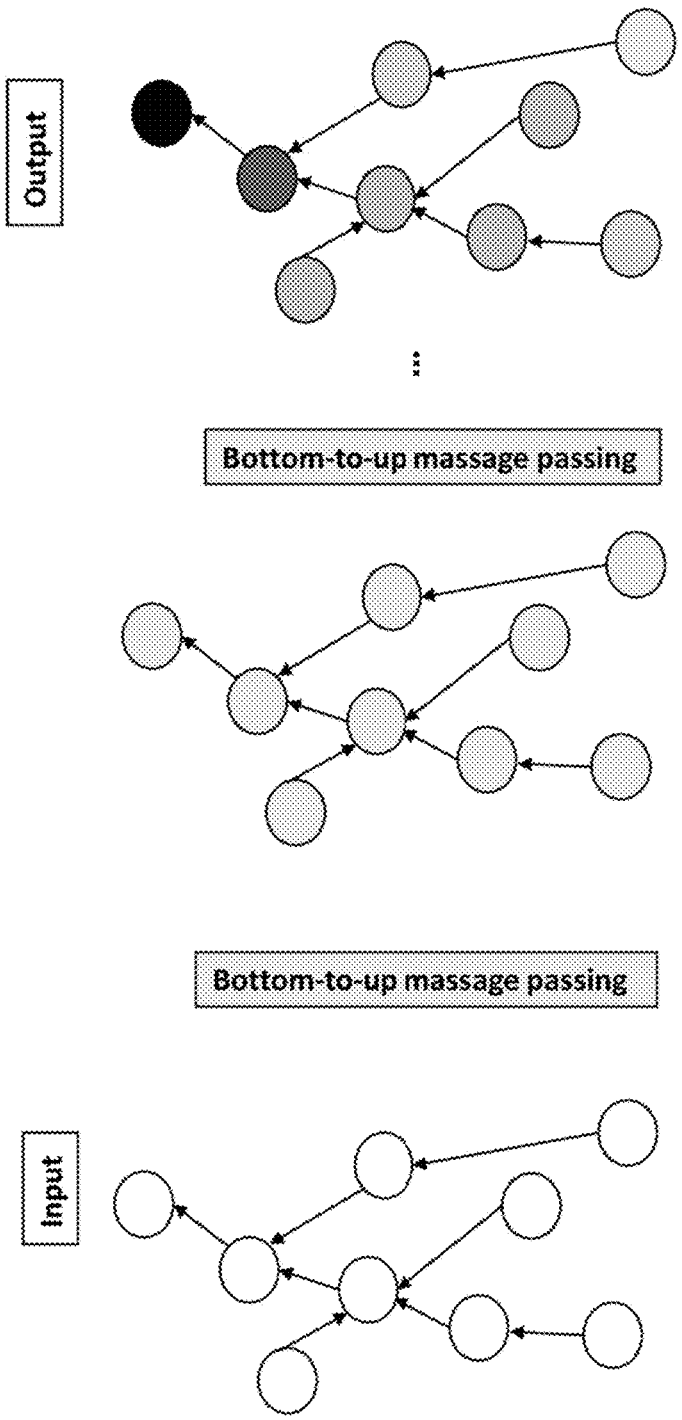
FIG. 4B is a schematic diagram illustrating a gate type of dynamic graph neural network according to an embodiment of the present disclosure.

FIG. 4B shows gate type of the dynamic graph neural network. A gate mechanism like Gated Recurrent Unit (GRU) or Long Short Term Memory (LSTM) can also be incorporated into the propagation step to improve the long-term propagation of information across the graph structure. In a directed tree structure, a child node can be a node that is connected to a parent node by an edge with a directionality in the direction of the child node. Thus, along an arterial system, a node in an artery may be a parent node to a child node in an arteriole. In such a system blood may flow from the node in the artery to the node in the arteriole, and consequently the node in the arteriole may be considered a "child" node, while the node in the artery may be considered a "parent node." The same principle can be applied to other tree structures including veins and lymphatic systems, among others. For example, if the edges of the graph are directional, by using gate mechanism, the parent node can selectively incorporate information from each child node for dynamic optimization of parameters of the disease quantification model. As an example, the gate may govern which information may be conveyed and what weight(s) may be set or adjusted. More particularly, each graph unit (could be a GRU or LSTM unit) contains input and output gates, a memory cell and hidden state. Instead of a single forget gate, each graph unit contains one forget gate for each child node, and the incoming edges indicate the child nodes of the node. The message passing could be bottom-to-up or up-to-bottom or both directions, see FIG. 4B for an example of bottom-to-up message passing. The graph unit could be any recurrent neural network (RNN) unit such as LSTM, GRU, convolutional LSTM (CLSTM) unit, convolutional GRU (CGRU) unit, etc.

Figure 5:
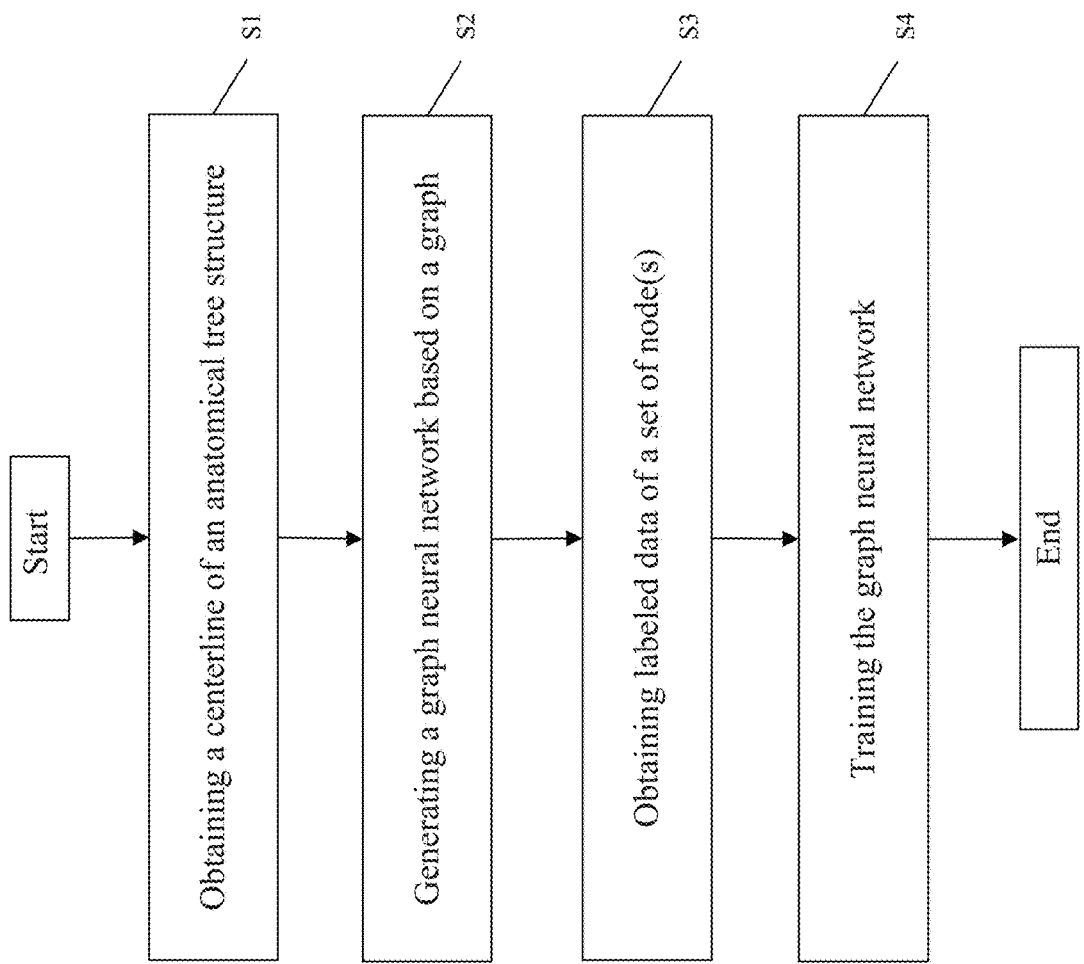
FIG. 5 illustrates a flowchart of an example method for disease quantification modeling according to an embodiment of present disclosure.

The flowchart of implementation of a method for disease quantification modeling of an anatomical tree structure is illustrated in FIG. 5. The method may include obtaining a centerline of an anatomical tree structure (Step S1). The method includes, at Step S2, generating a graph neural network including a plurality of nodes based on a graph, where each node corresponds to a centerline point and edges between the nodes of the graph neural network are defined by the centerline, with an input of each node being a disease related feature or a 2D/3D image patch for the corresponding centerline point and an output of each node being a disease quantification parameter. After the graph neural network is generated, labeled data (e.g., training data with ground-truth) of one or more nodes may be obtained, at Step S3. Then, at Step S4, the graph neural network may be trained by transferring information between the one or more nodes and other nodes based on the labeled data of the one or more nodes. The trained graph neural network has the optimized parameters (bias, weights, etc.) such that the optimal disease quantification model can be obtained. Particularly, the node number of the one or more nodes is less than a total number of the nodes in the graph neural network. According to an embodiment, the node number of the one or more nodes may be much less than a total number of the nodes in the graph neural network. Although Step S1 and Step S3 are shown as individual steps in FIG. 5, they can also be integrated into one step. As an example, upon a training image labeled with several ground truth values along its centerline is received, the centerline may be extracted and obtained meanwhile obtaining label date of the one or more nodes, which correspond to the already labeled centerline points.

According to embodiments of the disclosure, the one or more nodes include at least a first node at the inlet of the anatomical tree structure. Alternatively, the one or more nodes include the first node at the inlet of the anatomical tree structure and 1-3 additional nodes. According to an embodiment, only one additional node may be sufficient to train the graph neural network with the information passing mechanism. According to some embodiments, the graph neural network with less than or even about 1000 nodes may be well-trained based on only one labeled node or several labeled nodes. The present disclosure does not intend to limit the number of the nodes, and any number of nodes is possible. As a result, the disclosed dynamic graph neural network may learn how to propagate label information from labeled data towards the unlabeled data during the optimization, so as to obtain a well-trained graph neural network despite of the deficiency of labeled data points.

Figure 6:
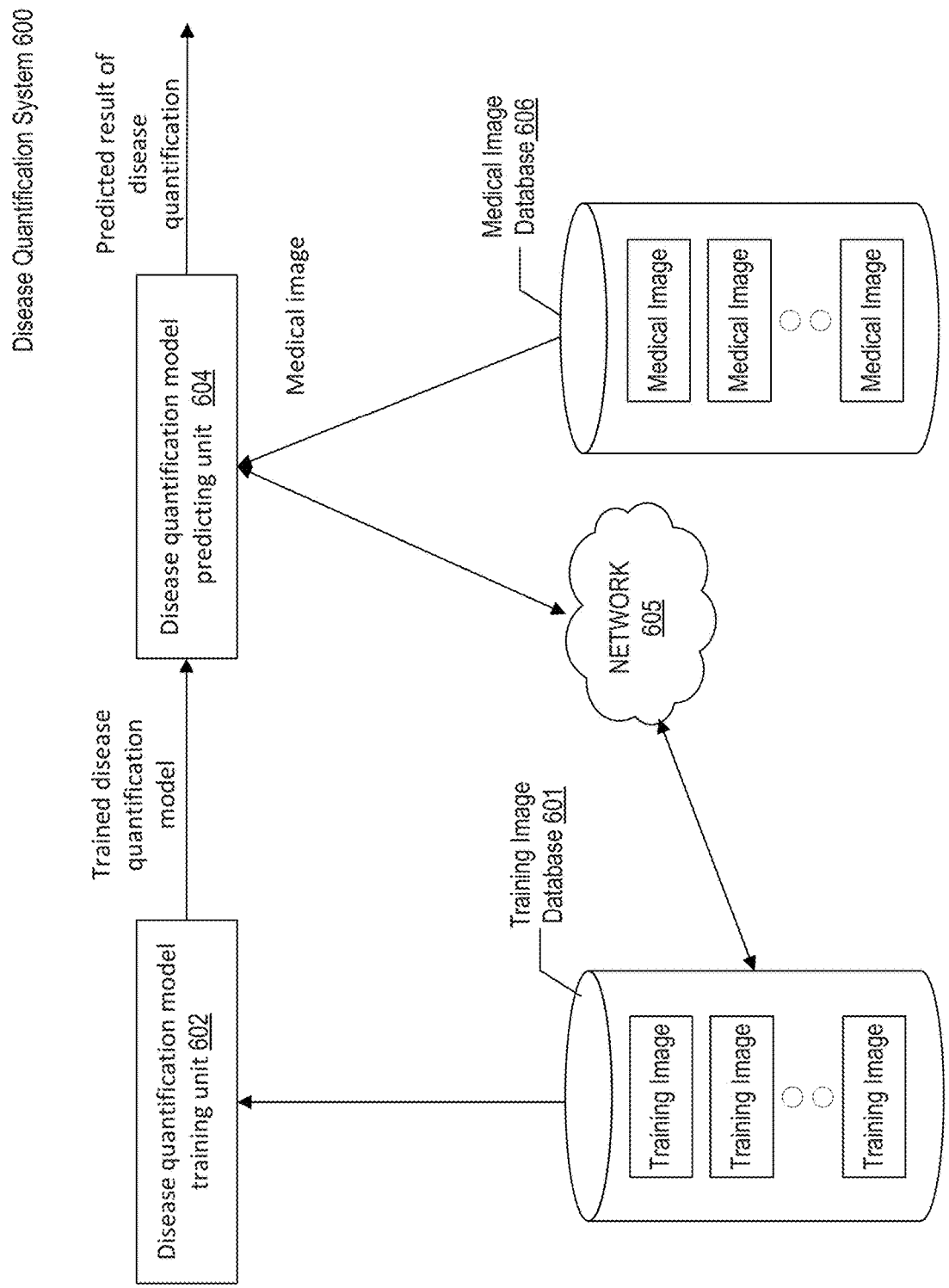
FIG. 6 depicts a schematic configuration diagram of disease quantification system according to an embodiment of present disclosure.

The training and prediction phases for disease quantification modeling will be described in detail with reference to FIG. 6, which illustrates an outline of implementations of disease quantification system 600. As shown, the system 600 may include a disease quantification model training unit 602 and a disease quantification predicting unit 604. The disease quantification model training unit 602 can acquire training image with ground truth values from a training image database 601 to train a disease quantification model, and as a result, can output the trained disease quantification model to the disease quantification predicting unit 604. The disease quantification predicting unit 604 may be communicatively coupled to a medical image database 606, and then may predict result(s) of disease quantification.

According to certain embodiments of the disclosure, training of the graph neural network may be performed by using gradient based methods, for example. In an implementation, the parameters of the graph neural network can be optimized by minimizing the objective function of the set of nodes during offline training. With only limited labeled data measured, the gradients and/or errors of the set of nodes can be transferred to the other nodes of the graph net through a back propagation approach for message or information passing. Thus, the structural information of the graph may be considered for a robust model. The disclosed architecture can, in certain embodiments, seamlessly integrate the information from the centerline points in the whole tree for more accurate prediction with only limited labeled data available. According to various embodiments, the objective function may be the means square error of the set of nodes. Alternatively, the objective function may be the weighted means square error of the set of nodes. In other words, the objective function may be defined by one skilled in the art as desired without departing from the spirit of the disclosure.

In some embodiments, the disease quantification predicting unit 604 may be communicatively coupled to the training image database 601 via network 605. In this manner, the predicted result of disease quantification obtained by the disease quantification predicting unit 604, upon confirmation by the radiologist or the clinician, may be fed back as training sample to the training image database 601 for future use. In this way, the training image database 601 may be augmented for expansion in scale in favor of better prediction results as well as improvement of accuracy of the model.

Figure 7:
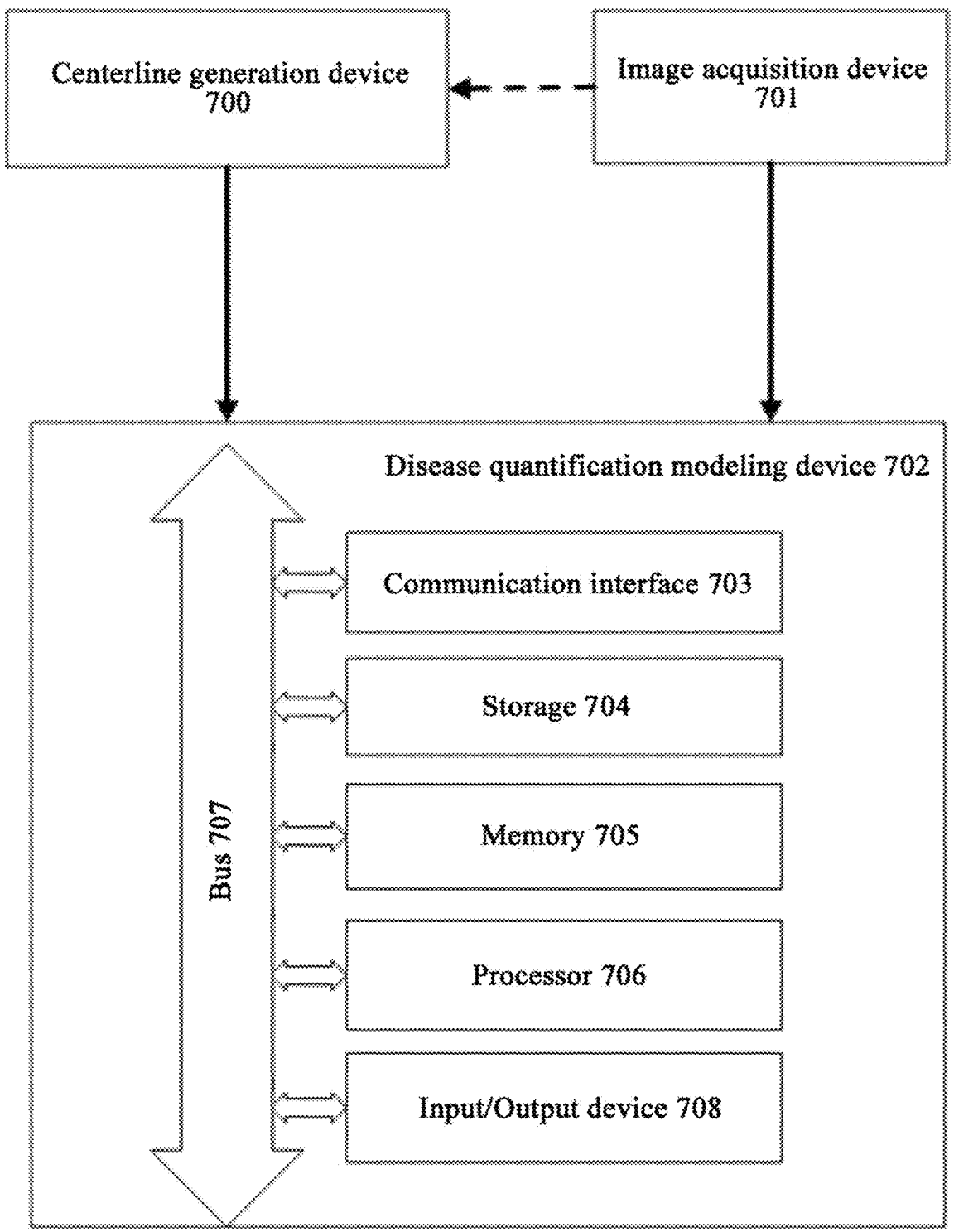
FIG. 7 depicts a block diagram illustrating an exemplary disease quantification system according to an embodiment of present disclosure.

A block diagram illustrating an exemplary disease quantification system according to an embodiment of present disclosure is described below with reference to FIG. 7. In some embodiments, the system may include a centerline generation device 700, an image acquisition device 701 and a disease quantification modeling device 702, for example. In some embodiments, the system may include only a disease quantification modeling device 702.

In some embodiments, the image acquisition device 701 may acquire and output an image by any type of imaging modalities, such as but not limited to CT, digital subtraction angiography (DSA), Magnetic Resonance Imaging (MRI), functional MRI, dynamic contrast enhanced MRI, diffusion MRI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging, and the like.

In some embodiments, the centerline generation device 700 is communicatively connected to the image acquisition device 701 and the disease quantification modeling device 702. According to an embodiment, the centerline generation device 700 may obtain the image directly or indirectly from the image acquisition device 701, conduct tree segment for the image, and then extract a centerline of the image, as illustrated in stages (a) and (b) of FIG. 3.

In some embodiments, the disease quantification modeling device 702 may be a dedicated computer or a general-purpose computer. The disease quantification modeling device 702 may be a hospital-customized computer for performing image acquisition and image processing tasks, for example, or a server in the cloud. As shown in FIG. 7, the disease quantification modeling device 702 may include a communication interface 703, a processor 706, a memory 705, a storage device 704, a bus 707, and an input/output device 708. For example, the communication interface 703, the processor 706, the memory 705, the storage device 704 and the input/output device 708 may be connected and communicated with one another.

In some embodiments, the communication interface 703 may include a network adapter, a cable connector, a serial connector, a USB connector, a parallel connector, a high-speed data transmission adapter (such as optical fiber, USB 3.0, Thunderbolt or the like), a wireless network adapter (such as WiFi adapter), telecommunication (3G, 4G/LTE, 5G, 6G and beyond). The disease quantification modeling device 702 may be connected to the centerline generation device 700, the image acquisition device 701 and other components. In some embodiments, the disease quantification modeling device 702 may receive the generated centerline from the centerline generation device 700 and medical image (e.g., a sequence of images of vessel) from the image acquisition device 701 via the communication interface 703.

In some embodiments, the memory 705/storage device 704 may be a non-transitory computer-readable medium or machine-readable medium such as read only memory (ROM), random access memory (RAM), a phase change random-access memory (PRAM), a dynamic random-access memory (DRAM) such as synchronous DRAM (SDRAM) or Rambus DRAM, a static random-access memory (SRAM), an Electrically-Erasable Programmable Read-Only Memory(EEPROM), flash memory, compact disc read-only memory (CD-ROM), digital versatile disk (DVD), magnetic storage device, etc., on which information or instructions which can be accessed and executed by a computer are stored in any format. In some embodiments, the trained graph neural network and model-related data may be stored in the storage device 704.

In some embodiments, the memory 705 may store computer-executable instructions, which, when executed by the processor 706, may perform the method for disease quantification modeling including the steps of: obtaining a centerline of an anatomical tree structure; generating a graph neural network including a plurality of nodes based on a graph where each node corresponds to a centerline point and edges between the nodes of the graph neural network are defined by the centerline, with an input of each node being a disease related feature or a 2D/3D image patch for the corresponding centerline point and an output of each node being a disease quantification parameter; obtaining labeled data of one or more nodes, the number of which is less than a total number of the nodes in the graph neural network; and training the graph neural network by transferring information between the one or more nodes and other nodes based on the labeled data of the one or more nodes.

The computer-executable instructions, when executed by the processor 706, may perform the steps of predicting disease quantification parameter for each test image. Particularly, the computer-executable instructions, when executed by the processor 706, may extract a test centerline of the test anatomical tree structure, generate a trained test graph neural network, extract a test disease related feature or a 2D/3D image patch for each test centerline point corresponding to test node, and predict the disease quantification parameters along the test centerline based on the extracted disease related features or 2D/3D image patches by utilizing the trained test graph neural network. The trained test graph neural network may be based on a test graph where each test node corresponds to a test centerline point and edges between the nodes of the graph neural network are defined by the test centerline. A test neural network unit for each test node may follow a graph-template setting of a neural network unit for each node of the trained graph neural network.

In some embodiments, the processor 706 may be a single-core or multi-core processing device that includes one or more general processing devices, such as a microprocessor, a central processing unit (CPU), a graphics processing unit (GPU), and the like. More specifically, the processor 706 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets.

The processor 706 may also be one or more dedicated processing devices such as application specific integrated circuits (ASICs), field programmable gate arrays (FPGAs), digital signal processors (DSPs), system-on-chip (SoC), and the like.

In some embodiment, the processor 706 may be communicatively coupled to the memory 705, and may be configured to obtain a centerline of an anatomical tree structure, to generate a graph neural network including a plurality of nodes based on a graph where each node corresponds to a centerline point and edges between the nodes of the graph neural network are defined by the centerline, with an input of each node being a disease related feature or a 2D/3D image patch for the corresponding centerline point and an output of each node being a disease quantification parameter, to obtain labeled data of one or more nodes, the number of which is less than a total number of the nodes in the graph neural network (for example, the one or more nodes with labeled data may be a subset of the nodes of the graph neural network), and to train the graph neural network by transferring information between the one or more nodes and other nodes based on the labeled data of the one or more nodes. According to some embodiments, the processor 706 is also configured to train the graph neural network as follows by using gradient based methods: to optimize the parameters of the graph neural network by minimizing the objective function of the set of nodes; and to transfer the gradients and/or errors of the set of nodes to the other nodes.

The input/output device 708 may be any input and output device such as keyboard, mouse, printer, display, scanner, touch panel, via which an operator may interface with the computer. In some embodiments, prediction result may be output from the input/output device 708 for presentation to a user such as clinician, patient, etc.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or non-recordable media.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

What is claimed is:

1. A computer implemented method for disease quantification modeling of an anatomical tree structure, comprising:
   obtaining a centerline of an anatomical tree structure from a training image;
   generating, by a processor, a graph neural network comprising a plurality of nodes based on a graph where each node corresponds to a centerline point and edges between the nodes of the graph neural network are defined by the centerline, with an input of each node being a disease related feature or an image patch for the corresponding centerline point and an output of each node being a disease quantification parameter;
   obtaining labeled data of one or more nodes, the number of which is less than a total number of the nodes in the graph neural network; and
   training, by the processor, the graph neural network by transferring information between the one or more nodes and other nodes based on the labeled data of the one or more nodes.

2. The method of claim 1, wherein the one or more nodes include at least a first node at the inlet of the anatomical tree structure.

3. The method of claim 1, further comprising:
   receiving a test image containing a test anatomical tree structure;
   extracting, by the processor, a test centerline of the test anatomical tree structure;
   generating, by the processor, a trained test graph neural network comprising a plurality of test nodes based on a test graph where each test node corresponds to a test centerline point and edges between the test nodes of the test graph neural network are defined by the test centerline, wherein a test neural network unit for each test node follows a graph-template setting of a neural network unit for each node of the trained graph neural network;
   extracting a test disease related feature or a test image patch for each test centerline point; and
   predicting disease quantification parameters along the test centerline based on the extracted test disease related features or test image patches by utilizing the trained test graph neural network.

4. The method of claim 1, wherein the disease related feature comprises at least one of a structural feature, an intensity feature, or a derived feature.

5. The method of claim 1, wherein the graph neural network comprises a graph convolutional neural network configured to perform a graph convolution operation for each node taking its neighbor nodes into account.

6. The method of claim 5, wherein the output of the graph convolutional neural network is a function of its input and an adjacent matrix, wherein the adjacent matrix is fixed and is determined by the centerline.

7. The method of claim 1, wherein each edge is undirected or directed, for propagating information between the nodes linked by the edge.

8. The method of claim 7, wherein the propagation of the information between the nodes implements a gate mechanism, wherein a plurality of graph units of the graph neural network correspond respectively to each of the nodes, with each graph unit containing input and output gates, a memory cell and a hidden state, wherein the graph unit comprises any one of Gated Recurrent unit (GRU), a Long Short Term Memory (LSTM) unit, convolutional LSTM (CLSTM) unit, or convolutional GRU (CGRU).

9. The method of claim 8, wherein each graph unit corresponds to a given node and contains one forget gate for each child node to the given node.

10. The method of claim 1, wherein the graph neural network is trained by:

optimizing parameters of the graph neural network by minimizing an objective function of the one or more nodes; and transferring the gradients or errors of the set of nodes to the other nodes.

11. A system for disease quantification modeling of an anatomical tree structure, comprising:

an interface configured to receive training images containing the anatomical tree structure;

a processor configured to, for each training image:

extract a centerline of the anatomical tree structure from the training image, generate a graph neural network comprising a plurality of nodes based on a graph where each node corresponds to a centerline point and edges between the nodes of the graph neural network are defined by the centerline, with an input of each node being a disease related feature or an image patch for the corresponding centerline point and an output of each node being a disease quantification parameter, obtain labeled data of one or more nodes, the number of which is less than a total number of the nodes in the graph neural network, and train the graph neural network by transferring information between the one or more nodes and other nodes based on the labeled data of the one or more nodes.

12. The system of claim 11, wherein the interface is further configured to receive test images containing test anatomical tree structures; and the processor is further configured to:

extract a test centerline of the test anatomical tree structure;

generate a trained test graph neural network comprising a plurality of test nodes based on a test graph where each test node corresponds to a test centerline point and edges between the nodes of the graph neural network are defined by the test centerline, wherein a test neural network unit for each test node follows a graph-template setting of a neural network unit for each node of the trained graph neural network;

extract a test disease related feature or an image patch for each test centerline point; and predict disease quantification parameters along the test centerline based on the extracted disease related features or image patches by utilizing the trained test graph neural network.

13. The system of claim 11, wherein the disease related feature comprises at least one of a structural feature, an intensity feature, or a derived feature.

14. The system of claim 11, wherein the graph neural network comprises a graph convolutional neural network configured to perform a graph convolution operation for each node taking its neighbor nodes into account.

15. The system of claim 14, wherein the output of the graph convolutional neural network is a function of its input and an adjacent matrix, wherein the adjacent matrix is fixed and is determined by the centerline.

16. The system of claim 11, wherein each edge is undirected or directed, for propagating information between the nodes linked by the edge.

17. The system of claim 16, wherein the propagation of the information between the nodes implements a gate mechanism, wherein a plurality of graph units of the graph neural network correspond respectively to each of the nodes, with each graph unit containing input and output gates, a memory cell and a hidden state, wherein the graph unit comprises any one of Gated Recurrent unit (GRU), a Long Short Term Memory (LSTM) unit, convolutional LSTM (CLSTM) unit, or convolutional GRU (CGRU).

18. The system of claim 17, wherein each graph unit corresponds to a given node and contains one forget gate for each child node to the given node.

19. The system of claim 11, wherein the processor is configured to train the graph neural network by optimizing the parameters of the graph neural network by minimizing the objective function of the set of nodes; and transferring the gradients and/or errors of the set of nodes to the other nodes.

20. A non-transitory computer readable medium storing instructions that, when executed by a processor, perform a method for disease quantification modeling of an anatomical tree structure, the method comprising:

obtaining a centerline of an anatomical tree structure;

generating a graph neural network comprising a plurality of nodes based on a graph where each node corresponds to a centerline point and edges between the nodes of the graph neural network are defined by the centerline, with an input of each node being a disease related feature or an image patch for the corresponding centerline point and an output of each node being a disease quantification parameter;

obtaining labeled data of one or more nodes, the number of which is less than a total number of the nodes in the graph neural network; and training the graph neural network by transferring information between the one or more nodes and other nodes based on the labeled data of the one or more nodes.

* * * * *